(12) United States Patent
Akay

(10) Patent No.: US 9,694,044 B2
(45) Date of Patent: Jul. 4, 2017

(54) THERMO-MODIFIED NUTSHELLS AND METHODS OF TREATING DIARRHEA, ADSORBING TOXINS, PROMOTING GROWTH AND IMPROVING THE OVERALL HEALTH

(71) Applicant: GLOBAL NUTRITECH BIOTECHNOLOGY LLC, Richmond, VA (US)

(72) Inventor: Veysel Akay, Kocaeli (TR)

(73) Assignee: GLOBAL NUTRITECH BIOTECHNOLOGY LLC, Richmond, VA (US)

( * ) Notice: Subject to any disclaimer, the term of this patent is extended or adjusted under 35 U.S.C. 154(b) by 241 days.

(21) Appl. No.: 14/492,221

(22) Filed: Sep. 22, 2014

(65) Prior Publication Data

US 2016/0082062 A1    Mar. 24, 2016

(51) Int. Cl.
*A61K 36/889* (2006.01)
*A61K 36/49* (2006.01)
*A61K 36/52* (2006.01)

(52) U.S. Cl.
CPC .......... *A61K 36/49* (2013.01); *A61K 2236/00* (2013.01)

(58) Field of Classification Search
CPC .... A61K 36/736; A61K 36/889; A61K 36/52; A61K 36/22; A61K 36/49
USPC ........................................ 424/735, 771, 776
See application file for complete search history.

(56) References Cited

U.S. PATENT DOCUMENTS

| | | | |
|---|---|---|---|
| 5,101,740 A | 4/1992 | Abril | |
| 6,033,573 A | 3/2000 | Toles et al. | |
| 6,045,834 A | 4/2000 | Howes et al. | |
| 7,048,937 B2 | 5/2006 | Dawson et al. | |
| 7,947,155 B1 | 5/2011 | Green et al. | |
| 8,227,235 B2 | 7/2012 | Skinner et al. | |
| 8,317,892 B1 | 11/2012 | Cheiky et al. | |
| 8,361,186 B1 | 1/2013 | Shearer et al. | |
| 8,558,044 B2 | 10/2013 | Smaidris | |
| 8,637,718 B2 | 1/2014 | Gupta et al. | |
| 2007/0202154 A1* | 8/2007 | Altom | A23K 10/37 424/442 |
| 2009/0232792 A1* | 9/2009 | Bicard-Benhamou | A61K 33/30 424/125 |
| 2011/0250303 A1* | 10/2011 | Nagashima | A61K 31/05 424/769 |

OTHER PUBLICATIONS

E. J. Bicknell et al., "Neonatal Calf Diarrhea", Arizona Ranchers' Management Guide, Animal Care and Health Maintenance, 1993, pp. 19-24.
Geof Smith, "Staying ahead of crypto", http://www.hoards.com/E_calf_heifer/CH04, 4 pages.
Achim Gerlach et al., "The use of biochar in cattle farming", Artikel weiterempfehlen, http://www.ithaka-journal.net/pflanzenkohle-in-der-rinderhaltung2lang=en, 7 pages.
Diarrheal Diseases, http://vetmed.iastate.edu/vdpam/new-vdpam-employees/food-supply-veterinary-medicine/swine/swine-diseases/diarrheal-diseases, 3 pages.
Michael Maenpaa et al., "Acrest Mobile Charcoal Kiln Final Report", Apr. 29, 2011, pp. 1-49.

\* cited by examiner

*Primary Examiner* — Chris R Tate
*Assistant Examiner* — Deborah Davis
(74) *Attorney, Agent, or Firm* — LeClairRyan, a professional corporation; Lisa E. Stahl

(57) ABSTRACT

Compositions comprising thermo-modified nutshells, for example hazelnut shells, are described herein. The compositions can also comprise one or more feed additives, pharmaceutically acceptable diluents and/or excipients. Also included are methods for producing the thermo-modified nutshell compositions, and methods for using the compositions to treat diarrhea and adsorb toxins as well as promote growth and improve the overall health in humans and other animals.

16 Claims, 1 Drawing Sheet

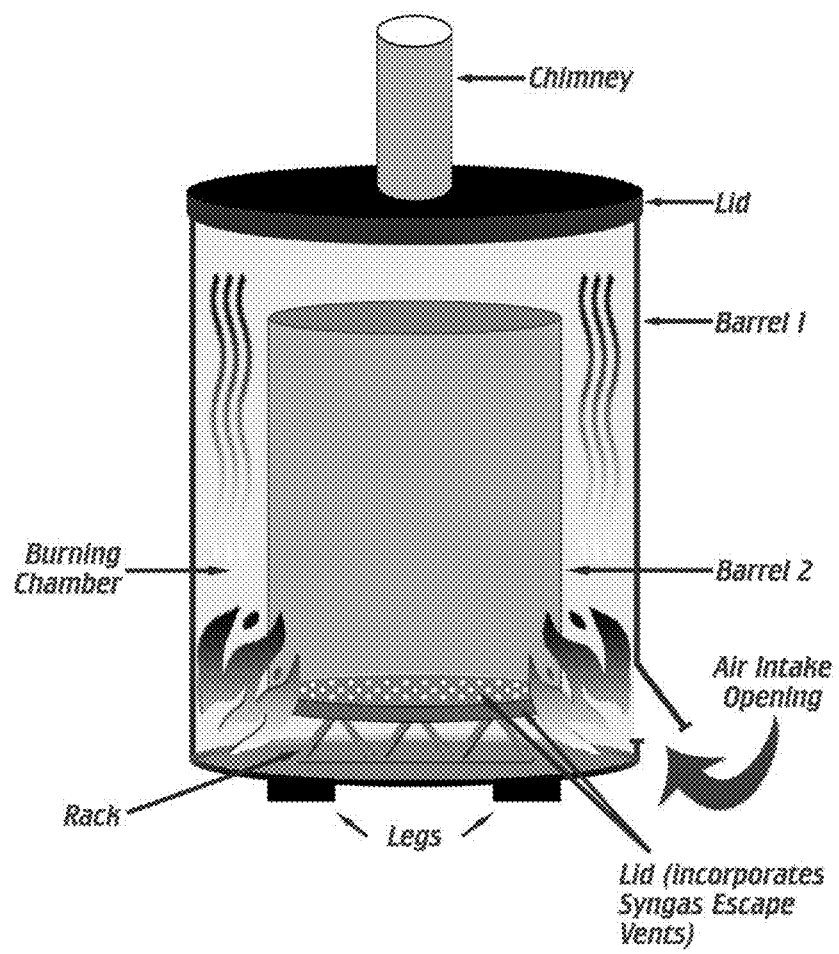

THERMO-MODIFIED NUTSHELLS AND METHODS OF TREATING DIARRHEA, ADSORBING TOXINS, PROMOTING GROWTH AND IMPROVING THE OVERALL HEALTH

FIELD

The present application is directed to compositions comprising thermo-modified nutshells, methods for making the same, and uses thereof for treating diarrhea and for adsorbing toxins, and for promoting growth and improving the overall health.

BACKGROUND

Diarrhea is a common disorder affecting both humans and other animals and can be caused by one or more infectious agents (e.g. viruses, bacteria and parasites), diseases affecting various organs (e.g. the intestine, liver, or adrenal system) and other predisposing factors (e.g. poor nutrition and environmental conditions). Chronic diarrhea is generally due to a number of factors which may occur separately or in combination, including hypersecretion of fluid and electrolytes in the stomach, small intestine and colon; a decrease in the absorption of nutrients; intestinal hypermotility and rapid transport through the digestive system. The loss of fluids and electrolytes often causes dehydration and electrolyte disturbances such as potassium deficiency or other salt imbalances, and can be fatal. Diarrhea is generally treated by rehydration therapy. Various anti-diarrheal drugs are known, one of the most common being antibiotics. However, antibiotic treatment has recently become more problematic, resulting in an increasing need for natural alternative non-antibiotic effective agents and methods for treating a wide range of diarrheal diseases in humans and other animals.

Mycotoxins, produced by mold, often contaminate animal feed and then enter the food chain, resulting in various health problems in both humans and other animals. Animal health is also adversely affected by enterotoxins from bacteria such as *Staphylococcus aureus, Streptococcus pyogenes* and *E. coli* that target the gastrointestinal tract causing diarrhea upon ingestion. To eliminate the negative effects of mycotoxins and enterotoxins on humans and other animals, a need exists for mycotoxin and enterotoxin binding agents that can be incorporated into human or other animal feed or provided as an oral supplement to inhibit absorption of the toxins into the human or other animal's bloodstream.

SUMMARY

Described herein are compositions comprising thermo-modified nutshells. The compositions can also comprise one or more feed additives, pharmaceutically acceptable diluents and/or excipients.

Also described herein are methods for producing the thermo-modified nutshell compositions, for treating diarrhea, for adsorbing toxins, and for promoting growth and improving the overall health. In certain embodiments, the nutshells comprise hazelnut shells.

BRIEF DESCRIPTION OF THE DRAWINGS

The FIGURE illustrates an example of a kiln that can be used to produce the thermo-modified nutshells.

DETAILED DESCRIPTION

The present application describes novel compositions comprising thermo-modified nutshells, and the methods for making the thermo-modified nutshell compositions, and methods for treating diarrhea and adsorbing toxins in a subject in need thereof by administering a therapeutically effective amount of the present composition. Treatment with the present compositions can also promote growth and improve the overall health, especially in young animals. The compositions can be administered orally as a dietary supplement or via incorporation into food products for humans or other animals.

The thermo-modified nutshells can be produced by pyrolysing nutshells. Pyrolysis is a thermochemical decomposition of organic material, such as biomass, at elevated temperatures under non-oxidizing conditions. Pyrolysis differs from other high-temperature processes like combustion and hydrolysis in that it usually does not involve reactions with oxygen, water, or any other reagents. Because essentially no oxygen is present, the organic material does not combust. Instead, the chemical compounds (i.e. cellulose, hemicellulose and lignin) that make up the material thermally decompose. However in practice it may not be possible to achieve a completely oxygen-free atmosphere, thus a small amount of oxidation can occur.

Pyrolysis of biomass generally produces three products: solids (e.g. thermo-modified nutshells), liquids (bio-oil) and gas (syngas). The proportion of these pyrolysis products depends on several factors, including the composition of the biomass and the process parameters. Processes that use slower heating rates are called slow pyrolysis, in which the solid fraction is usually the major product. Various methods for pyrolysis of biomass are known in the art (e.g., U.S. Pat. Nos. 5,101,740; 7,947,155; 8,361,186; and 8,558,044).

The organic material used to produce the thermo-modified nutshells described in this application comprises any nutshell, including, but not limited to, shells from one or more of the following: hazelnuts, almonds, walnuts, pecans, macadamia nuts, Brazil nuts, pistachios, cashews, or coconuts. Generally, the nutmeats have been removed from the shells prior to heat treatment (pyrolysis).

The nutshells can be pyrolysed at temperatures between 100° C. and 1000° C. (e.g. between 200° C. and 800° C.; 350° C. and 750° C.; 400° C. and 700° C.; or 400° C. and 600° C.), for a time ranging between 1 second and 24 hours (e.g. between 0.5 hours and 12 hours; 1 hour and 6 hours; or 2 hours and 4 hours), without oxygen. The resulting thermo-modified nutshells are rich in fixed carbon, volatile matters, and ash. After pyrolysis, the thermo-modified nutshells can contain, for example, 0-20% moisture, 20-90% fixed carbon, 5-70% volatile matters, and 0.5-40% ash on a dry matter basis. Another example is 3-12% moisture, 74-80% fixed carbon, 18-24% volatile matters, and 3.5-4.5% ash on a dry matter basis. The material can be ground to a particle size of less than 10 mm (e.g. less than 5 mm, less than 2 mm, less than 1 mm, or less than 100 micron) before and/or after heat treatment.

Generally, the thermo-modified nutshells are not treated (e.g. with acids, hydroxides, or 900° C. water steam) to become "activated carbon" or "activated charcoal."

The present compositions can be formulated with only thermo-modified nutshells, or, alternatively, one or more feed additives, diluents, excipients or carriers can be added. The composition may comprise one or more substances that can assist in its application or storage stability, such as stabilizers, preservatives, binders, adjuvants, buffer substances, disintegrating agents, lubricants, glidants, sweetening agents, or flavoring agents. The composition may also comprise one or more additional active agents, such as toxin adsorbents (e.g. bentonites, montmorillonites, hydrated sodium calcium aluminium silicates and yeast cell wall extracts); probiotics (e.g. *E. faecium, L. plantarum, L. acidophilus, L. brevis, L. casei, B. subtilis, B. longum, B. thermophilum* and *B. linhenformis*); prebiotics (e.g. mannanologosaccharides and fructooligosaccharides); electrolytes (e.g. salts (including sodium bicarbonate and potassium chloride)) and steroidal surfactants (e.g. sapogenin).

In some embodiments, the composition is formulated for oral administration as a dietary supplement, such as formulation in dosage unit form, i.e. physically discrete units containing a predetermined quantity of thermo-modified nutshells for ease of administration and uniformity of dosage (e.g. pills, capsules, tablets, lozenges, and the like). In some embodiments the composition can be administered as a component of a feed composition (e.g. pellets, granules, powders, semi-solid slurries, and liquids) for oral ingestion.

As noted above, the thermo-modified nutshell compositions can be used to treat diarrhea, adsorb toxins, and promoting growth and improve the overall health in a subject in need thereof. "Subject", as used herein, refers to an animal, and can include any animal such as animals of the homo sapien (e.g. humans), porcine (e.g. pigs), bovine (e.g. cattle), avian (e.g. chickens, turkeys, ducks, and quails), caprine (e.g. goats), ovine (e.g. sheep), equine (e.g. horses), lapine (e.g. rabbits), feline (e.g. cats) or canine (e.g. dogs) species. "Subject" also refers to any animal used in aquaculture (e.g. fish, crustaceans, and mollusks). The animal subject can be in any stage of development from birth to maturity. In certain embodiments, the animal is a human. In other embodiments, the animal is a non-human animal.

"Treatment" or "treating" refers to complete elimination as well as to any clinically or quantitatively measurable prevention, reduction, amelioration, or improvement in the condition being treated. Generally, a lower dosage can be used as a preventative measure.

A "therapeutically effective amount" means the amount of a composition that, when administered to a subject for treating diarrhea, is sufficient to effect a desirable treatment for the diarrhea. The "therapeutically effective amount" will vary depending on the particular composition, the diarrhea and its type and severity, and the species, condition, age, weight, etc., of the subject to be treated. A "therapeutically effective amount" need not result in a complete cure, but may provide partial relief of one or more symptoms or retard the progression of the condition.

As used herein, the term "diarrhea" includes any diarrheal disease, such as diarrhea caused by one or more pathogens (e.g. parasites, bacteria, protozoa, and viruses); toxic agents created by food or feed spoilage; nutritional factors (e.g. excess mineral salts, excess protein, food sensitivities, allergic agents in food, and indigestible or poor quality food components); medications (e.g. antibiotics); environmental stressors (e.g. heat, chilling, shipment of animals, and pollutants from air or water); and physiological disorders (e.g. those of the digestive tract, pulmonary/circulatory system, liver, kidneys, and pancreas).

Examples of common diarrheal diseases (and their causative agents) include *Enteric colibacillosis* (*Escherichia coli*); *Rotaviral enteritis* (*Rotavirus*, usually group A); Transmissible gastroenteritis (Coronavirus); *Clostridium*-associated enterotoxemia (*Clostridium difficile* and *Clostridium perfringens* type A); *Salmonellosis* (usually *Salmonella* serotypes *Choleraesuis, Typhimurium,* or *Heidelberg*); Cryptosporidiosis (*Cryptosporidium*); Coccidiosis (*Coccidia* parasites); Swine dysentery (*Brachyspira hyodysenteriae*); Proliferative enteritis (*Lawsonia intracellularis*); and Whipworm infection (*Trichuris suisdiarrheal*).

As noted above, the thermo-modified nutshell compositions can also be administered to humans or other animals as a dietary supplement or via incorporation into human foodstuffs or animal feed (e.g. feed additives, premixes, pastes or gels, milk or milk replacers) or any other route of administration, to bind or adsorb mycotoxins and/or enterotoxins. Examples of relevant mycotoxins include Aflatoxins, Zearalenone, Trichothecenes, Fumonisins, and Ochratoxins. Examples of relevant enterotoxins include toxins produced by *Clostridium difficile, Clostridium perfringens, Vibrio cholerae, Staphylococcus aureus, Yersinia enterocolitica, Shigella dysenteriae,* and *Rotavirus*.

The thermo-modified nutshell compositions can be administered in an amount effective to bind and inactivate mycotoxins and/or enterotoxins present in the human or animal feed and/or in the digestive system of the subject. Various methods for testing toxin-binding efficacy are known in the art (e.g. U.S. Pat. No. 6,045,834). Treating humans or other animals with the compositions can prevent or minimize absorption or uptake of the toxins by the animal, resulting in prevention, amelioration, or a decrease in the incidence of toxin-associated disorders.

As also noted above, the thermo-modified nutshell compositions can also be administered to humans or other animals as a dietary supplement or via incorporation into human foodstuffs or animal feed (e.g. feed additives, premixes, pastes or gels, milk or milk replacers) or any other route of administration, in an amount effective to promote growth and improve the overall health.

The dosage regimen for treating diarrhea, for adsorbing toxins and/or for promoting growth and improving the overall health is selected in accordance with a variety of factors, including the species, age, weight, production stage, sex, and medical condition of the subject, the route of administration, pharmacological considerations such as the activity, efficacy, pharmacokinetic and toxicology profiles of the particular composition used, and whether the composition is administered as part of a combination of active agents. Exemplary dosages include providing from 0.1 g to 500 g thermo-modified nutshells per head per day (e.g. dosages of 0.2 g to 500 g, 0.2 g to 400 g, 0.5 g to 200 g, 1 g to 100 g, or 5 g to 50 g thermo-modified nutshells per head per day). Other exemplary dosages include providing from 0.01 g to 1 g per kg of body weight (e.g. dosages of 0.02 g to 0.5 g or 0.05 g to 0.8 g per kg of body weight). In some embodiments the thermo-modified nutshell composition is administered in foodstuffs for animals. The thermo-modified nutshell composition can be admixed with the feed at any concentration, such as concentrations of 0.1 kg to 50 kg of thermo-modified nutshells per ton of feed (e.g. concentrations of 0.2 kg to 20 kg, 0.5 kg to 15 kg, or 1 kg to 10 kg thermo-modified nutshells per ton of feed).

The doses may be administered in single or divided applications. The doses may be administered once, or application may be repeated. Application may be repeated, for example, one or more times a day, weekly or with each meal. For some indications more frequent dosing such as hourly application may be employed. The composition may be administered before, during, or immediately following the onset of symptoms, or later, for example when the condition to be treated is diagnosed. The composition may also be administered as a preventative measure, i.e. prophylactically, and for promoting growth and improving the overall health.

As used herein, the singular forms "a", "an" and "the" include plural referents unless the context clearly dictates otherwise.

The publications disclosed herein are provided solely for their disclosure prior to the filing date of the present application. Nothing herein should be construed as an admission that the present disclosure is not entitled to antedate such publication by virtue of prior disclosure. Further, the dates of publication provided may be different from the actual publication dates, which may need to be independently confirmed. All publications, patents, patent applications and other references cited herein are hereby incorporated by reference in their entirety.

While the disclosure has been described in detail with reference to certain embodiments thereof, it will be apparent to one skilled in the art that various changes can be made, and equivalents employed, without departing from the scope of the disclosure. In addition, the following examples are illustrative only and should not be considered as limiting the disclosure in any way.

EXAMPLES

Example 1

Hazelnut shells were modified using the kiln shown in the FIGURE Ten kg of hazelnut shells were placed in Barrel 2, and then Barrel 2 was placed into Barrel 1 upside down. The shells were heated 3 hrs to reach a temperature of 500° C. in the absence of oxygen by burning wood in the Burning Chamber of Barrel 1. The heat-treated shells in Barrel 2 were then allowed to cool to room temperature before opening and exposing sample to oxygen. Ten kg of hazelnut shells yielded 3.3 kg of thermo-modified nutshells, which represents 33% by total weight. The sample was ground by passing it through a 2 mm screen.

Example 2

At a dairy farm, forty-five Holstein calves receiving milk replacer and showing signs of diarrhea (scouring) were treated to determine the efficacy of the thermo-modified nutshells obtained in Example 1. Calves were kept in individual calf pens and fed milk replacer twice a day. Diagnostic test kits from BioX Diagnostic (Jemelle, Belgium) were used to diagnose the cause of diarrhea from fecal samples. The diarrhea in the majority of the calves tested (40 out of 45) was caused by one or more of the following pathogens: *Cryptosporidia, Esherichia coli, Rotavirus, Coronavirus* and *Clostridium perfringens*. When calves showed signs of diarrhea, the thermo-modified nutshells were added to the milk replacer in the amount of 10 g in the morning feeding and 10 g in the evening feeding (20 g/day). Treatment was continued daily until there were no signs of diarrhea. The results of the treatment are shown in Table 1 below. These results demonstrate that the thermo-modified nutshells were very effective against diarrhea caused by *Cryptosporidia, Esherichia coli, Rotavirus, Coronavirus* and/or *Clostridium perfringens* in calves.

TABLE 1

Effect of Thermo-Modified Hazelnut Shells Treatment on Diarrhea Caused by Different Pathogens in Dairy Calves

| Causes of Diarrhea | Number of Calves | Average Age of Calves (Days) | Length of Treatment (Days) | Results* |
|---|---|---|---|---|
| *Cryptosporidia* | 12 | 9.4 | 2.5 | 1 |
| *Cryptosporidia* | 6 | 9.8 | 3 | 2 |
| *Esherichia coli* | 7 | 7.9 | 2.6 | 1 |
| *Esherichia coli* | 1 | 8 | 3 | 2 |
| *Rotavirus* | 1 | 10 | 3 | 1 |
| *Cryptosporidia + Rotavirus* | 1 | 13 | 3 | 2 |
| *Cryptosporidia + Clostridium perfringens* | 1 | 8 | 3 | 2 |
| *Cryptosporidia + Clostridium perfringens* | 1 | 7 | 2 | 1 |
| *Rotavirus + Esherichia coli* | 1 | 5 | 3 | 1 |
| *Rotavirus + Esherichia coli* | 1 | 3 | 3 | 2 |
| *Rotavirus + Clostridium perfringens* | 1 | 8 | 2 | 2 |
| *Rotavirus + Coronavirus* | 4 | 3.8 | 2.5 | 1 |
| *Rotavirus + Coronavirus* | 2 | 5.5 | 2.5 | 2 |
| *Rotavirus + Cryptosporidia + Clostridium perfringens* | 1 | 7 | 2 | 1 |
| Not Known | 5 | 8.6 | 1.9 | 1 |

*Stool Fluidity was graded on a scale of one (1) through four (4):
1. NORMAL—Firm but not hard. Original form is distorted slightly after dropping to floor and settling.
2. SOFT—Does not hold form, piles but spreads slightly.
3. RUNNY—Spreads readily to about 6 mm depth.
4. WATERY—Liquid consistency, splatters.

Example 3

At a dairy farm different from that of Example 2, fifteen Holstein calves receiving milk and showing signs of diarrhea (scouring) were treated using the protocol described above in Example 2. Similar to above, the results (shown below in Table 2) demonstrate that the thermo-modified nutshells were very effective against diarrhea caused by *Cryptosporidia* or *Esherichia coli* in dairy calves.

TABLE 2

Effect of Thermo-Modified Hazelnut Shells Treatment on Diarrhea Caused by Different Pathogens in Dairy Calves

| Causes of Diarrhea | Number of Calves | Average Age of Calves (Days) | Length of Treatment (Days) | Results* |
|---|---|---|---|---|
| *Cryptosporidia* | 13 | 8 | 5.5 | 1 |
| *Esherichia coli* | 2 | 10 | 4 | 1 |

*Stool Fluidity was graded on a scale of one (1) through four (4):
1. NORMAL—Firm but not hard. Original form is distorted slightly after dropping to floor and settling.
2. SOFT—Does not hold form, piles but spreads slightly.
3. RUNNY—Spreads readily to about 6 mm depth.
4. WATERY—Liquid consistency, splatters.

The invention claimed is:
1. A method for treating diarrhea in a subject in need thereof comprising administering to said subject an effective amount of a composition comprising thermo-modified nutshells,
   wherein said thermo-modified nutshells are obtained by pyrolysing one or more nutshells selected from the group consisting of hazelnuts, almonds, walnuts, pecans, macadamia nuts, brazil nuts, pistachios, cashews, coconuts, and any combinations thereof, at a temperature between 100 C. and 1,000 C. for between 1 second and 24 hours, without oxygen.

2. The method of claim 1, wherein the diarrhea is associated with one or more condition selected from the group consisting of *Enteric colibacillosis, Rotaviral enteritis*, Transmissible gastroenteritis, *Clostridium*-associated enterotoxemia, *Salmonellosis*, Cryptosporidiosis, Coccidiosis, Swine dysentery, Proliferative enteritis, Whipworm infection, and any combinations thereof.

3. The method of claim 1, wherein the subject is (i) an animal selected from the group consisting of animals of the homo sapien, porcine, bovine, avian, caprine, ovine, equine, lapine, feline and canine species, or (ii) an animal selected from the group consisting of fish, crustaceans and mollusks.

4. The method of claim 1, wherein the composition is administered as a dietary supplement, as a component of a human or other animal feed, or as a combination thereof.

5. The method of claim 1, wherein the composition is administered at a dosage of from 0.1 g to 100 g thermo-modified nutshells per day.

6. The method of claim 1, wherein the composition is administered at a dosage of from 0.01 g to 1 g thermo-modified nutshells per kg of body weight.

7. The method of claim 1, wherein the composition is administered as a component of a human or other animal feed, and wherein the thermo-modified nutshells are present in the feed at a concentration of from 0.1 kg to 50 kg of thermo-modified nutshells per ton of feed.

8. The method of claim 1, wherein the diarrhea is caused by a toxin selected from the group consisting of mycotoxins, enterotoxins, and combinations thereof.

9. The method of claim 8, wherein the mycotoxins are selected from the group consisting of Aflatoxins, Zearalenone, Trichothecenes, Fumonisins, Ochratoxins, and any combinations thereof.

10. The method of claim 8, wherein the enterotoxins are selected from the group consisting of toxins produced by *Clostridium difficile, Clostridium perfringens, Vibrio cholerae, Staphylococcus aureus, Yersinia enterocolitica, Shigella dysenteriae, Rotavirus*, and any combinations thereof.

11. The method of claim 1, wherein the nutshells comprise hazelnut shells.

12. The method of claim 1, wherein the composition further comprises one or more components selected from the group consisting of diluents, excipients, carriers, and any combinations thereof.

13. The method of claim 1, wherein the composition further comprises one or more additional active agents.

14. The composition of claim 13, wherein the one or more additional active agents are selected from the group consisting of toxin adsorbents, probiotics, prebiotics, electrolytes, steroidal surfactants, and any combinations thereof.

15. The method of claim 1, wherein said thermo-modified nutshells comprise 0-20% moisture, 20-90% fixed carbon, 5-70% volatile matters, and 0.5-40% ash on a dry matter basis.

16. The method of claim 1, wherein said thermo-modified nutshells do not comprise activated charcoal.

* * * * *